(12) United States Patent
Zollinger et al.

(10) Patent No.: US 10,117,894 B2
(45) Date of Patent: Nov. 6, 2018

(54) MAGNESIUM DELIVERY SYSTEM

(71) Applicant: NFuse, LLC, Owings Mills, MD (US)

(72) Inventors: Emily Offutt Zollinger, Owings Mills, MD (US); Ann Offutt Ahl, Kennett Square, PA (US)

(73) Assignee: NFUSE, LLC, Owings Mills, MD (US)

( * ) Notice: Subject to any disclaimer, the term of this patent is extended or adjusted under 35 U.S.C. 154(b) by 0 days.

(21) Appl. No.: 15/615,033

(22) Filed: Jun. 6, 2017

(65) Prior Publication Data

US 2017/0354677 A1 Dec. 14, 2017

Related U.S. Application Data

(60) Provisional application No. 62/348,516, filed on Jun. 10, 2016.

(51) Int. Cl.
| | | |
|---|---|---|
| *A61K 33/08* | (2006.01) | |
| *A61K 47/02* | (2006.01) | |
| *A61K 47/36* | (2006.01) | |
| *A61M 35/00* | (2006.01) | |
| *A61K 47/10* | (2017.01) | |
| *A45D 34/00* | (2006.01) | |
| *A61K 9/00* | (2006.01) | |
| *A61K 47/46* | (2006.01) | |

(52) U.S. Cl.
CPC ............ *A61K 33/08* (2013.01); *A61K 9/0014* (2013.01); *A61K 47/02* (2013.01); *A61K 47/10* (2013.01); *A61K 47/36* (2013.01); *A61K 47/46* (2013.01); *A61M 35/003* (2013.01)

(58) Field of Classification Search
CPC ...... A45D 34/041; A61K 33/08; A61K 47/02; A61K 47/10; A61K 47/36; A61K 47/46; A61K 9/0014
See application file for complete search history.

(56) References Cited

U.S. PATENT DOCUMENTS

| | | | |
|---|---|---|---|
| 4,659,560 A | 4/1987 | Bews | |
| 5,512,274 A | 4/1996 | Phinney | |
| 9,314,412 B2 | 4/2016 | Phinney | |
| 2008/0317873 A1 | 12/2008 | Schmit | |
| 2014/0018750 A1 | 1/2014 | Pagliaro | |
| 2014/0271517 A1 | 9/2014 | Phinney | |

FOREIGN PATENT DOCUMENTS

| | | | | |
|---|---|---|---|---|
| EP | 0468564 A2 | 1/1992 | | |
| WO | WO 2016/018474 | * | 2/2016 | .............. C08L 71/02 |
| WO | WO 2007/095261 | * | 8/2017 | |

OTHER PUBLICATIONS

Nasanta (magnesium Deodorant http://nasanta.com.au/product-features (Feb. 27, 2015)).*
"DeodoMom—Hypoallergenic Lotion Deodorant Roll-On", Blue Herbs N.A., Web, accessed Jun. 9, 2017.
"3 oz. MagneSoothe Deodorant", MG12, Web, accessed Jun. 9, 2017.
"Top Natural Deodorants", Green Tidings, Web, accessed Jun. 9, 2017.
"Sensitive Skin Deodorant Stick", Schmidt's Naturals, Web, accessed Jun. 9, 2017.
"Happy Pits Natural Deodorant Sensitive Stick—Baking Soda Free", Primal Pit Paste, Web, accessed Jun. 9, 2017.
"Baking Soda Free Dedorant Cream", Meow Meow Tweet, Web, accessed Jun. 9, 2017.
"Charcoal + Magnesium Mineral-Enriched Deodorant", Schmidt's Naturals, Web, accessed Jun. 9, 2017.
"Aluminum-Free MoM (Milk of Magnesia) Roll-on Deodorant", The People's Pharmacy, Web, accessed Jun. 9, 2017.
"PiperWai Natural Deodorant", PiperWai, Web, accessed Jun. 9, 2017.
"Magnesium deodorant for men", Nasanta Magnesium Deodorant, Web, accessed Jun. 9, 2017.
"Magnesium deodorant for women", Nasanta Magnesium Deodorant, Web, accessed Jun. 9, 2017.
"Gnger Rose Roll-On Deodorant", Honestly pHresh, Web, accessed Jun. 9, 2017.
Kass et al., "Effect of transdermal magnesium cream on serum and urinary magnesium levels in humans: A pilot study", PLOS, Apr. 12, 2017.
Waring et al., "Report on Absorption of magnesium sulfate (Epsom salts) across the skin", University of Birmingham, Oct. 2015.
C. Heard, "In Vitro Transdermal Delivery of Magnesium", Cardiff University, Oct. 25, 2011.
Watkins et al., "A pilot study to determine the impact of transdermal magnesium treatment on serum levels and whole body CaMg ratios", The Nutrition Practitioner, Spring 2010.
Engen et al., "Effects of transdermal magnesium chloride on quality of life for patients with fibromyalgia: a feasibility study", Journal of integrative medicine, Sep. 1, 2015, vol. 8, No. 5, abstract.
Chandrasekaran et al., "Permeation of Topically Applied Magnesium Ions Through Human Skin Is Facilitated by Hair Follicles", Magnesium Research, Jun. 1, 2016, vol. 29, No. 2, abstract.
"Sore & Tired", Miscopeto LLC, Label.
"Olive Tree Natural Deodorant", Olive Tree Body Care, Web, accessed Jun. 16, 2017.
"Detoxium", Lucas Meyer Cosmetics, Web, accessed Jun. 16, 2017.
"Organic Magnesium Oil Body Cream 8oz", La Caron, Web, accessed Jun. 16, 2017.
"Magnesium Gel With Sea Mineral Extract Joint & Muscle Formula", Oriel, Label.
"Magnesium Gel With Sea Mineral Extract Dry Skin Formula", Oriel, Label.

* cited by examiner

*Primary Examiner* — Anna R Falkowitz
(74) *Attorney, Agent, or Firm* — W&C IP

(57) ABSTRACT

A roll-on product, including magnesium hydroxide; propanediol; glycerin and *glycine soja* (soybean), is advantageously used as a deodorant and/or for transdermal magnesium delivery to the human body. Combinations of a magnesium source (especially magnesium hydroxide), with propanediol, and with glycerin and *glycine soja* (soybean) are advantageous for transdermal delivery of magnesium to the body via a roll-on product, a stick, a spray, a lotion, etc. Magnesium deficiency is addressed via products easily used by an ordinary consumer for dermal application.

11 Claims, No Drawings

MAGNESIUM DELIVERY SYSTEM

FIELD OF THE INVENTION

The invention relates to ameliorating magnesium deficiency in a human, and more particularly, transdermal delivery of magnesium to a human body especially via underarm skin.

BACKGROUND OF THE INVENTION

Over 50% of Americans' diets are deficient in magnesium. For many people, dietary intake of magnesium is insufficient due to low intake of magnesium rich foods, low magnesium content in drinking water, and unpleasant laxative effects of orally ingested magnesium.

Bathing in Epsom salts have been known conventionally as an approach in which the body can receive some magnesium through bathing, but such a bathing-based approach is time-consuming, and can be impractical or impossible for, or rejected by, some people.

Magnesium chloride sprays have been known to cause itching and burning on the skin which impedes their popularity and effectiveness for widespread use remedying magnesium deficiency.

There has been an unmet need for easy-to-use, non-oral products readily and quickly useable by people deficient in magnesium.

SUMMARY OF THE INVENTION

The present inventors recognized that there was a problem of there being, conventionally, no magnesium-delivery product in a form of a personal care product useable at least once daily, and they solved that problem by inventing magnesium permeation technology, beginning with magnesium permeation technology that optimizes absorption of magnesium to the body through the underarms.

An objective of the invention is to provide a transdermal delivery system which administers an alkaline magnesium compound to the underarm skin such as through a roll-on, a stick, a spray, a gel, a cream, a lotion, etc. The process of the alkaline magnesium compound reacting with moisture, acids, and salts present on and around the underarm skin causes magnesium ions to be released and available for absorption into the skin.

Another objective of the invention is to provide technology in which a magnesium compound (such as magnesium hydroxide, magnesium oxide, magnesium sulfate, magnesium chloride, or a combination thereof) is used alone or in combination with one or more ingredients that increase permeation of magnesium ions into the underarm skin.

A further objective of the invention is to provide methodology for administering, to the body, a therapeutic dose of elemental magnesium at a ratio between 5-60%, more preferably 10-60%, of total composition weight.

In a preferred embodiment, the invention provides a deodorant that controls odor and delivers magnesium to the body.

The invention in another preferred embodiment provides a transdermal magnesium supplement for use under the arms.

In another preferred embodiment the invention provides a transdermal magnesium supplement, such as for use in health care and wellness fields, for physicians and health care professionals to prescribe to populations struggling with magnesium deficiency.

The invention also includes a preferred embodiment that provides a transdermal magnesium supplement in health care and wellness fields for physicians and health care professionals to prescribe to enhance effectiveness of conventional treatments for various health conditions including but not limited to asthma, depression, diabetes, arrhythmia and heart failure, migraine headache, osteoporosis and restless leg syndrome.

In another preferred embodiment the invention provides a combined magnesium replacement system and deodorant for chemotherapy patients who are at risk for hypomagnesemia due to side effects of chemotherapy drugs.

The invention in another preferred embodiment provides a combined magnesium replacement system and deodorant for athletes during and after workouts to restore magnesium levels and speed muscle recovery.

In another preferred embodiment the invention provides a transdermal magnesium supplement for premenopausal and menopausal relief.

The invention in another preferred embodiment provides a natural deodorant for people concerned about possible link of aluminum, parabens, phthalates, synthetic fragrances, and other harmful chemicals to breast cancer and Alzheimer's disease.

In another preferred embodiment, the invention provides a back pain reliever and/or provides muscle pain relief and/or provides neck pain relief.

In another preferred embodiment, the invention provides a sleep aid that can be applied one hour prior to bedtime.

The invention in a preferred embodiment provides a roll-on product, comprising a container inside which is disposed a quantity of a solution comprising: water; a magnesium component (such as, e.g., magnesium hydroxide; magnesium sulfate; magnesium chloride; combinations thereof; etc.); propanediol; and glycerin and *glycine soja* (soybean), such as, e.g., inventive roll-on products wherein the solution consists of water, magnesium hydroxide, propanediol, glycerin and *glycine soja* (soybean), and the one or more plant extracts, and only the solution is inside the container; inventive roll-on products wherein the solution has an intradermal magnesium delivery characteristic of a quantity of magnesium being delivered to a human to whom the solution has been applied to dermis; inventive roll-on products wherein the solution has the intradermal magnesium delivery characteristic when the solution has been applied underarm; and other inventive roll-on products.

In another preferred embodiment, the invention provides a solution for transdermal magnesium delivery, comprising: water; a magnesium compound (such as, e.g., magnesium hydroxide; magnesium sulfate; magnesium chloride; combinations thereof; etc.); propanediol; glycerin and *glycine soja* (soybean), such as, e.g., an inventive solution applicable to human dermis via roll-on from a roll-on container; an inventive solution applicable to human dermis via spraying from a container; an inventive solution applicable to human dermis via a solution-soaked patch; an inventive solution applicable to human dermis via a lotion; etc.

The invention in another preferred embodiment provides a method of transdermal delivery of magnesium hydroxide, comprising swiping a human underarm with a roll-on and thereby delivering onto the dermis a solution comprising water, magnesium hydroxide, propanediol, and glycerin and *glycine soja* (soybean) (such as, e.g., a swiping step wherein swiping a right underarm and a left underarm of a human delivers about 300 mg magnesium hydroxide onto the dermis of the human).

In another preferred embodiment, the invention provides a roll-on product, comprising a container inside which is disposed a quantity of a solution comprising: water; propanediol; and glycerin and *glycine soja* (soybean), such as, e.g., inventive roll-on products further comprising a magnesium compound (such as, e.g., magnesium hydroxide; magnesium chloride; magnesium sulfate; combinations thereof; etc.).

The invention in another embodiment provides a roll-on product, comprising a solid stick comprising: a magnesium compound (such as, e.g., magnesium hydroxide; magnesium sulfate; magnesium chloride; combinations thereof; etc.); propanediol; and glycerin and *glycine soja* (soybean).

DESCRIPTION OF A PREFERRED EMBODIMENT OF THE INVENTION

For the inventive transdermal magnesium delivery, it will be appreciated that a critical ingredient in any formulation is always a magnesium component. The magnesium component, and indeed each and every component used in the formulation to be used for transdermal magnesium delivery to the body, must be safe for application to human skin. Examples of a magnesium component are, e.g., magnesium hydroxide; magnesium sulfate; magnesium chloride; combinations thereof; etc. Magnesium hydroxide is preferred for use as the magnesium component, such as, e.g., a magnesium hydroxide-containing formulation that is deliverable via a roll-on product; a magnesium hydroxide slurry (such as, e.g., a magnesium hydroxide slurry in which magnesium content to water content is approximately 60% Mg:40% $H_2O$); comprising magnesium hydroxide in a form of, or derived from, FloMag magnesium hydroxide slurry; magnesium hydroxide particles having a median particle size of about 3.0 micron; magnesium hydroxide particles having a size in a range of 1.0-4.0 micron; a magnesium hydroxide slurry characterized by specific surface area of about 10 $m^2/g$; a magnesium hydroxide slurry characterized by specific surface area in a range of 9-20 $m^2/g$; etc.

Flowmag® (Flowmag H®) (commercially available from Martin Marietta) is a magnesium hydroxide slurry that is most preferred to use for an inventive transdermal magnesium delivery formulation. Flowmag H® has the following characteristics: On a slurry basis, the Mg(OH)$_2$ contained is 7.7 lb/gal typically, with 8.0 maximum and 7.0 minimum. On a dry solids basis: the Mg(OH)$_2$ is 98.8 wt % typically, 985% minimum, with CaO typically 0.6 wt %, maximum 0.8%; $SiO_2$ typically 0.20 wt %, maximum 0.35; $Fe_2O_3$ typically 0.10 wt %, 0.21 maximum. Flomag H® has a median particle size of 3.0 micron typically, maximum 4.0, minimum 1.0, a specific surface area of 10 $m^2/g$ typically, 20 maximum and 9 minimum, and is characterized by 3.21 acres/gallon typically, 3.5 maximum and 3.0 minimum.

An example of a roll-on product is, e.g., a roll-on product comprising a container and a rolling ball that occupies an opening of the container.

In a case of delivery to the skin via roll-on container, a solution of Flowmag®, preferably is further combined with one or both of a propanediol component, and a glycerin and *glycine soja* (soybean) component.

A magnesium component (such as a magnesium hydroxide; a magnesium sulfate; a magnesium chloride; combinations thereof; etc.) also can be formulated into a spray delivery system, a stick delivery system, a lotion delivery system, etc. Combining the magnesium component (such as, e.g., magnesium hydroxide; magnesium sulfate; magnesium chloride; combinations thereof; etc.) with one or both of a propanediol component, and a glycerin and *glycine soja* (soybean) component, is preferred for all transdermal delivery systems, such as solutions used in roll-on containers, solutions used in spray delivery containers, solids used as sticks, lotions, etc.

A preferred example of a glycerin and *glycine soja* (soybean) component for use in the invention is a composition comprising glycerin in a range of about 64-82% and *glycine soja* in a range of about 18-36% (such as LysoFix® liquid—glycerin and *glycine soja*—product #018047 manufactured by Kemin Industries Inc.). The most preferred example of the glycerin and *glycine soja* is LysoFix®.

A preferred example of a propanediol component for use in the invention is 1-3 propanediol, such as Zemea® propanediol manufactured by Dupont Tate & Lyle BioProducts.

The present inventors sometimes use the term "Triangle Ingredients" herein to mean a combination of (1) a magnesium component; (2) a propanediol component and (3) a glycerin and *glycine soja* (soybean). Transdermal application of the Triangle Ingredients, variously formulated, is most preferred for delivering magnesium to the body, including use of formulations comprising only the Triangle Ingredients and formulations comprising the Triangle Ingredients with one or more other optional ingredients.

An amount of magnesium hydroxide or magnesium component in an inventive formulation preferably is in a range of 10-70% by weight, more preferably in a range of 45-55% by weight.

An amount of propanediol in an inventive formulation preferably is in a range of 10-30% by weight, more preferably in a range of 17.5-22.5% by weight.

An amount of glycerin (and) *glycine soja* (soybean) seed extract in an inventive formulation preferably is a range of 1-10% by weight, more preferably 3.5-7.5% by weight.

Examples of a ratio of magnesium hydroxide:glycerin (and) *glycine soja* (soybean) seed extract:propanediol in formulations according to the invention are, e.g., in a range of about 9:4:1 to 11:4:1, in a range of about 10:3.5:1 to 10:4.5:1, etc. A most preferred example of a ratio of magnesium hydroxide:glycerin (and) *glycine soja* (soybean) seed extract:propanediol in formulation is 10:4:1.

Examples of ingredients optionally contained in formulations for transdermal delivery of magnesium according to the invention are, e.g., essential oils (such as, e.g., lemon, *eucalyptus*, lavender, *mentha piperita* (peppermint) oil, *rosmarinus offinalis* (rosemary) leaf oil, *cymbopogon flexuosus* (lemongrass) oil, combinations thereof, etc.); seed extract; plant extract; *matricaria recuita* (chamomile); flower extract; heptyl undecylenate; acacia senegal gum; sodium bicarbonate; xanthan gum; combinations thereof; etc.

Preferably, a solution to be used for transdermal delivery of magnesium according to the invention avoids, or minimizes, usage of aluminum, parabens, phthalates, artificial preservatives, propylene glycol, synthetic fragrance, and zinc salts. Most preferably, a solution to be used for transdermal delivery of magnesium according to the invention contains no aluminum, no parabens, no phthalates, no artificial preservatives, no propylene glycol, no synthetic fragrance, and no zinc salts.

The invention may be appreciated with reference to the following examples, without the invention being limited to these examples.

Example 1 (Transdermal Delivery Systems that Administer an Alkaline Magnesium Compound with a pH in the Range of 9 to 11 to the Underarm Skin)

Example 1A

A method for a transdermal delivery system which administers the alkaline magnesium compound to the underarm skin through one of the following: a roll-on, a stick, a spray, a gel, or a cream. The process of the alkaline magnesium compound reacting with moisture, acids, and salts present on and around the underarm skin causes magnesium ions to be released and available for absorption into the skin.

Example 1B

A transdermal delivery system wherein the magnesium compound is magnesium hydroxide, magnesium oxide, magnesium sulfate, magnesium chloride, or a combination thereof. The preferred magnesium hydroxide is a hydrolyzed slurry with a ratio of magnesium to water greater than 25%.

Example 1B1

A preferred formulation includes Flowmag®, a hydrolyzed magnesium hydroxide slurry (60% magnesium hydroxide to 40% water) manufactured and sold by Martin Marietta using a patented manufacturing and blending process that results in a chemical reaction to create a highly stable solution with superior surface spread and reactivity.

Example 1B2

Another preferred formulation includes Flogel®, a low viscosity, magnesium hydroxide gel (29-33% magnesium hydroxide to 67-71% water) manufactured and sold by SPI Pharma.

Example 1C

Methods according to Examples 1-1B2, wherein the elemental magnesium is at a ratio between 10-60% of total composition weight.

Example 1D

Transdermal delivery of magnesium according to Examples 1-1A, wherein the absorption of magnesium through the underarm is enhanced using a transdermal delivery system comprising one or more of: (a) active transdermal delivery agent, first means of transport of magnesium through skin; (b) solvent and permeation enhancer, second means for enhancing the permeation of magnesium through the underarm skin; (c) essentials oils, third means for enhancing permeability of skin; (d) fourth means for binding the magnesium compound with (a) the active transdermal delivery agent, (b) a solvent and permeation enhancer and (c) essential oils with permeation enhancing properties into a single transdermal delivery system applied to the underarm skin.

Example 1E

A transdermal delivery system, including as a means for active transdermal delivery one or more of the following vegetable oils: Lysofix®, a soybean seed extract, a sunflower oil, jojoba oil, coconut oil, almond oil, ground nut oil, shea butter oil, corn oil, babassu oil, castor oil, Clark A oil, cotton seed oil, linseed oil, mustard oil, olive oil, palm oil, peanut oil, safflower oil, sesame oil, soybean oil, sunflowerseed oil, and wheat germ oil.

Example 1E1

A preferred formulation includes Lysofix®, a soybean seed extract manufactured and sold by Kemin Industries. Lysofix® has been found by the inventors to be superior to other permeation enhancers which are currently commercially available.

Example 1F

A transdermal delivery system, including for enhancing the permeation of magnesium through the underarm skin one or more of the following: propandiol, propylene glycol (1,2-propanediol) and butylene glycol (1,3-/1,4-butanediol).

Example 1G

A transdermal delivery system, including for enhancing the permeation of magnesium through the underarm skin one or more of the following essential oils: peppermint, *eucalyptus*, clove, ylang ylang, wintergreen, tulsi, rose, black cumin, tea tree, lemongrass, grapefruit, orange, lemon, bergamot, tangerine, basil, nutmeg, thyme, geranium, cinnamon, bay leaf, rosemary, camphor, niaouli, and carraway.

Example 1H

A transdermal delivery system for magnesium delivery, in which is included a water soluble gum of one or more of the following: agar, arabic, arabic senegal, carob, CMC, carrageenans, ghatti, guar, karaya, kadaya, locust bean, tragacanth, xanthan gum.

Example 2 (Early Formulations)

Example 2A

Water 10-85%
$Mg(OH)_2$ 10-60%
Aloe Vera 0-40%
Glycerin 5-15%
Sodium Bicarbonate 0-3%
Xanthan Gum 0-1%
Essential Oils 0-2%

Example 2B

Water 10-85%
MgO 10-60%
Aloe Vera 0-40%
Glycerin 5-15%
Sodium Bicarbonate 0-3%
Xanthan Gum 0-1%
Essential Oils 0-2%

Example 2C

Water 10-85%
$Mg(OH)$, 5-50%
MgO 5-50%
Aloe Vera 0-40%

Glycerin 5-15%
Sodium Bicarbonate 0-3%
Xanthan Gum 0-1%
Essential Oils 0-2%

Example 2D

Water 10-85%
Mg(OH), 1-50%
MgSO$_4$ 0-10%
MgO 1-50%
Aloe Vera 0-40%
Glycerin 5-15%
Sodium Bicarbonate 0-3%
Xanthan Gum 0-1%
Essential Oils 0-2%

Example 2E

Flowmag® 15-90%
MgSO$_4$ 0-10%
Water 0-50%
Aloe Vera 0-40%
Glycerin 5-15%
Sodium Bicarbonate 0-3%
Xanthan Gum 0-1%
Essential Oils 0-2%

Example 2F

Flogel® 30-90%
MgSO$_4$ 0-10%
Water 0-50%
Aloe Vera 0-40%
Glycerin 5-15%
Sodium Bicarbonate 0-3%
Xanthan Gum 0-1%
Essential Oils 0-2%

Example 2G

Water 25-75%
MgSO$_4$ 20-50%
Mg(OH), 0-20%
Alcohol 0-40%
Witch Hazel 0-45%
Aloe Vera 0-35%
Essential Oils 0-2%

Example 3 (Preferred Formulations)

Example 3A

Water 10-90%
Mg(OH), 10-90%
LysoFix® 1-10%

Example 3B

Flowmag® 90-99%
LysoFix® 1-10%

Example 3C

Flogel® 90-99%
LysoFix® 1-10%

Example 3D

Water 10-90%
MgO 10-90%
LysoFix® 1-10%

Example 3E

Water 10-90%
MgO 1-50%
Mg(OH), 1-50%
LysoFix® 1-10%

Example 3F

Water 10-90%
Mg(OH)$_2$ 10-90%
Propanediol 10-70%
LysoFix® 1-10%

Example 3G

Water 10-90%
Mg(OH)$_2$ 10-90%
Propanediol 10-70%
LysoFix® 1-10%
Essential Oils 0-2%

Example 3H

Water 0-50%
Flowmag® 15-90%
Propanediol 10-70%
LysoFix® 1-10%
Essential Oils 0-2%

Example 3I

Water 0-50%
Flogel® 30-90%
Propanediol 10-70%
LysoFix® 1-10%
Essential Oils 0-2%

Example 3J

Water 10-90%
Mg(OH)$_2$ 10-90%
Propanediol 10-70%
LysoFix® 1.5-10%
Arabic Senegal Gum 0-1%
Xanthan Gum 0-1%
Essential Oils 0-2%

Example 3K

Water 10-90%
Mg(OH), 10-90%
Propylene Glycol 10-70%
LysoFix® 1.5-10%
Arabic Senegal Gum 0-1%
Xanthan Gum 0-1%
Essential Oils 0-2%

Example 3L water 10-90%
magnesium hydroxide 10-90% propanediol 10-70%
glycerin & *glycine soja* (soybean) seed extract 2-10%
essential oils 0-2%

Example 3M water 10-90%
magnesium hydroxide 10-90%
propanediol 10-70%
glycerin & *glycine soja* (soybean) seed extract 2-10%
sodium bicarbonate 0-5%
essential oils 0-2%

Example 4 (Most Preferred Formulations)

Example 4A

Water 33.5-43.5%
Mg(OH)$_2$ 25-35%
Propanediol 17.5-22.5%
LysoFix® 3.5-5%
Emollient 2.5-5%
Sodium Bicarbonate 0.5-1%
Gum 0.5-1.5%
Essential Oils 0-2%

Example 4B

Water 15-20%
FloMag® 45-55%
Propanediol 17.5-22.5%
LysoFix® 3.5-5%
Emollient 2.5-5%
Sodium Bicarbonate 0.5-1%
Gums 0.5-1.5%
Essential Oils 0-2%

Example 4C

Water 36-46%
Flogel 63-73%
Propanediol 17.5-22.5%
LysoFix® 3.5-5%
Emollient 2.5-5%
Sodium Bicarbonate 0.5-1%
Gums 0.5-1.5%
Essential Oils 0-2%

Example 4D water 10-90%
magnesium hydroxide 10-90%
propanediol 10-70%
essential oils and plant extracts 0-20%

Example 4E water 10-90%
magnesium hydroxide 10-90%
propanediol 10-70%
glycerin & *glycine soja* (soybean) seed extract 2-10%
essential oils and plant extracts 0-20%

Example 4F water 10-90%
magnesium hydroxide 10-90%
propanediol 10-70%
LysoFix 0.5-7.5%
essential oils and plant extracts 0-20%

Example 4G water 10-90%
magnesium hydroxide 10-90%
propanediol 10-70%
LysoFix 0.5-7.5%
emollient 0-10%
essential oils and plant extracts 0-20%

Example 4H water 5-20%
FlowMag 45-55%
Propanediol 17.5-22.5%
LysoFix 3.5-7.5%
emollient 0-10%
essential oils 0-15%

Example 4I water 5-20%
FlowMag 17%-60%
Magnesium Chloride 5-40%
Propanediol 17.5-22.5%
LysoFix 3.5-7.5%
emollient 0-10%
essential oils and plant extracts 0-20%

Example 4J water 5-20%
FlowMag 17%-60%
Magnesium Sulfate 5-40%
Propanediol 17.5-22.5%
LysoFix 3.5-7.5%
emollient 0-10%
essential oils and plant extracts 0-20%

Example 4K water 5-20%
FlowMag 17%-30%
Magnesium Chloride 20-35%
Propanediol 17.5-22.5%
LysoFix 3.5-7.5%
emollient 0-10%
essential oils and plant extracts 0-15%

Example 4L water 5-20%
FlowMag 17%-30%
Magnesium Sulfate 20-35%
Propanediol 17.5-22.5%
LysoFix 3.5-7.5%
emollient 0-10%
essential oils and plant extracts 0-15%

Example 4M

FlowMag 50%
Water 0-18%
Propanediol 20%

LysoFix 5%
LexFeel Natural 5%
essential oils and plant extracts 1-20%

Example 4N

FlowMag 50%
Water 10-18%
Propanediol 20%
LysoFix 5%
LexFeel Natural 5%
essential oils 2-10%

Example 5 (Rosemary-Mint)

A rosemary-mint magnesium roll-on having no aluminum, no zinc salts, no parabens, no phthalates, no propylene glycol, no synthetic fragrance, no preservatives, having as ingredients:
water
magnesium hydroxide,
propanediol,
glycerin (and) *glycine soja* (soybean) seed extract
*matricaria reculita* (chamomile) flower extract
heptyl undecylenate
acacia senegal gum
sodium bicarbonate
*mentha piperita* (peppermint) oil
*rosmarinus offinalis* (rosemary) leaf oil
xanthan gum
*cymbopogon flexuosus* (lemongrass) oil

Example 5A (Unscented)

An unscented magnesium roll-on having no aluminum, no zinc salts, no parabens, no phthalates, no propylene glycol, no synthetic fragrance, no preservatives, having as ingredients:
magnesium hydroxide
water
propanediol
glycerin and *glycine soja* (soybean)
heptyl undecylenate
Sodium Bicarbonate
xanthan gum
Acacia Gum

Example 5B (Citrus)

A citrus magnesium roll-on having no aluminum, no zinc salts, no parabens, no phthalates, no propylene glycol, no synthetic fragrance, no preservatives, having as ingredients:
magnesium hydroxide
water
propanediol
glycerin and *glycine soja* (soybean)
heptyl undecylenate
Chamomile Extract
Acacia Gum
Grapefruit
Sodium Bicarbonate
Sweet Orange
xanthan gum
Lemongrass
Geranium

Example 5C (Lavender)

A lavender magnesium roll-on having no aluminum, no zinc salts, no parabens, no phthalates, no propylene glycol, no synthetic fragrance, no preservatives, having as ingredients:
magnesium hydroxide
water
propanediol
glycerin and *glycine soja* (soybean)
heptyl undecylenate
lavender
acacia gum
sodium bicarbonate
clary sage
xanthan gum
bergamot
lemongrass

Example 6 (Relief of Back Pain)

A formulation comprising the Triangle Ingredients was used transdermally for relieving back pain. Transdermal application preferably is onto the back where the pain is experienced.

Example 6A (Relief of Muscle Aches)

A formulation comprising the Triangle Ingredients was used transdermally for relieving muscle aches. Transdermal application is preferably onto the skin near where the muscle aches are experienced.

Example 6B (Relief of Neck Pain)

In this example, a formulation comprising the Triangle Ingredients is used for relieving neck pain. Transdermal application is preferably onto the skin of the neck.

Example 7

In this example, a formulation for use in a roll-on product comprises one or more of:
seed extract;
*matricaria recuita* (chamomile);
flower extract;
heptyl undecylenate;
acacia senegal gum;
sodium bicarbonate;
*mentha piperita* (peppermint) oil;
*rosmarinus offinalis* (rosemary) leaf oil;
xanthan gum; and
*cymbopogon flexuosus* (lemongrass) oil.

Example 8

A formulation for use in a roll-on product comprising (by weight):
water in a range of about 15-20%;
magnesium hydroxide in a range of about 45-55%;
propanediol in a range of about 17.5-22.5%;
glycerin and *glycine soja* (soybean) in a range of about 3.5-5%;
plant-derived components in a range of about 3.5-9.5%.

Example 8A

The formulation of Example 8, comprising (by weight):
Flomag 49.5-50%
propanediol 17.5-22.5%
glycerin and *glycine soja* (soybean) 3.5-5%.

Example 9 (Unscented Formulation)

A formulation for a roll-on product consisting of (by weight):

| | |
|---|---|
| Flowmag | 49.5% |
| Water | 18.5% |
| Zemea | 20.0% |
| Lysofix | 5.0% |
| Lexfeel Natural | 5.0% |
| Sodium Bicarbonate | 1.0% |
| Keltrol | 0.3% |
| Acacia Gum | 0.7% |

Example 10 (Rosemary Mint Formulation)

A formulation for a roll-on product consisting of (by weight):

| | |
|---|---|
| Flowmag | 50.0% |
| Water | 12.7% |
| Zemea | 20.0% |
| LysoFix | 5.0% |
| LexfeelNatural | 5.0% |
| Chamomile Extract | 5.0% |
| Acacia Gum | 0.7% |
| Peppermint | 0.4% |
| Rosemary | 0.3% |
| Sodium Bicarbonate | 0.5% |
| Keltrol | 0.3% |
| Lemongrass | 0.1% |

Example 11 (Citrus Formulation)

A formulation for a roll-on product consisting of (by weight):

| | |
|---|---|
| Flowmag | 50.00% |
| Water | 11.50% |
| Zemea | 20.00% |
| LysoFix | 5.00% |
| LexfeelNatural | 5.00% |
| Chamomile Extract | 5.00% |
| Acacia Gum | 0.70% |
| Grapefruit | 0.70% |
| Sodium Bicarbonate | 0.50% |
| Sweet Orange | 0.50% |
| Keltrol | 0.30% |
| Lemongrass | 0.50% |
| Geranium | 0.40% |

Example 12 (Lavender Formulation)

A formulation for a roll-on product consisting of (by weight):

| | |
|---|---|
| Flowmag | 50.0% |
| Water | 16.9% |
| Zemea | 20.0% |
| LysoFix | 5.0% |
| LexfeelNatural | 5.0% |
| Lavender | 0.9% |
| Acacia Gum | 0.7% |
| Sodium Bicarbonate | 0.5% |
| Clary Sage | 0.3% |
| Keltrol | 0.3% |
| Bergamot | 0.2% |
| Lemongrass | 0.2% |

Example 13

In this example, for computing an amount of magnesium to be included in a formulation comprising the Triangle Ingredients, an estimate is used that an amount of absorbed magnesium is in a range of about 10-25%, which corresponds to an amount of magnesium applied to the skin but NOT absorbed (such as due to being washed-off) being in a range of about 75-90%.

Example 14 (Magnesium Sulfate)

In this example, a formulation comprising magnesium sulfate is as follows:
magnesium sulfate 1-10%
water 15-20%
FloMag® 45-55%
Propanediol 17.5-22.5%
LysoFix® 3.5-5%

Example 15 (Formulation Process)

A preferred formulation process is as follows:
1) Mix/shake magnesium hydroxide continuously.
2) Mix magnesium hydroxide with water (preferably for about 5 minutes).
3) Add glycerin (and) *glycine soja* (soybean) seed extract and mix (preferably for about 5 minutes).
4) Mix propanediol with acacia and xanthan gums and mix (preferably for about 5 minutes) and add to the magnesium-containing mixture and mix (preferably for about 5 minutes).
5) Add sodium bicarbonate, mix (preferably for about 5 minutes)
6) Add heptyl undecylenate (and essential oils), mix (preferably for about 10 minutes)

Example 15A

In this example, steps 1-4 of Example 15 are performed, without performing steps 5-6.

Example 16

A sprayable solution for transdermal magnesium delivery is prepared, comprising:
water
magnesium sulfate
propanediol
glycerin & *glycine soja* (soybean)

Example 16A

A sprayable solution for transdermal magnesium delivery according to Example 16 is prepared, containing no magnesium hydroxide.

The descriptions of various embodiments of the present invention have been presented for purposes of illustrations, but are not intended to be exhaustive. Many modifications and variations will be apparent to those of ordinary skill in the art without departing from the scope and spirit of the described embodiments.

What we claim as our invention is:

1. A roll-on product, comprising a container inside which is disposed a quantity of a solution comprising:
   water;
   a magnesium-containing compound selected from the group consisting of magnesium hydroxide; magnesium chloride; and magnesium sulfate;
   propanediol;
   glycerin and *glycine soja* (soybean),
wherein the product comprises a magnesium hydroxide slurry in which magnesium content to water content is approximately 60% Mg:40% $H_2O$ by weigh.

2. The roll-on product of claim 1, wherein the glycerin and *glycine soja* is a form of a glycerin/*glycine soja* composition consisting of glycerin in a range of 64-82% by weigh thereof and *glycine soja* in a range of 18-36% by weigh thereof.

3. The roll-on product of claim 1, further comprising a rolling ball that occupies an opening of the container.

4. The roll-on product of claim 1, wherein the solution contains no component selected from the group consisting of: aluminum; parabens; phthalates; artificial preservatives; propylene glycol; synthetic fragrance; and zinc salts.

5. The roll-on product of claim 1, further comprising one or more selected from the group consisting of:
   seed extract;
   *matricaria recuita* (chamomile);
   flower extract;
   heptyl undecylenate;
   acacia senegal gum;
   sodium bicarbonate;
   *mentha piperita* (peppermint) oil;
   *rosmarinus offinalis* (rosemary) leaf oil;
   xanthan gum; and
   *cymbopogon flexuosus* (lemongrass) oil.

6. The roll-on product of claim 1, further comprising one or more plant extracts.

7. A roll-on product, comprising a container inside which is disposed a quantity of a solution, wherein the solution consists of water; magnesium hydroxide; propanediol; glycerin and *glycine soja* (soybean); and the one or more plant extracts, and only the solution is inside the container.

8. The roll-on product of claim 1, wherein the solution has an intradermal magnesium delivery characteristic of a quantity of magnesium being delivered to a human to whom the solution has been applied to dermis.

9. The roll-on product of claim 8, wherein the solution has the intradermal magnesium delivery characteristic when the solution has been applied underarm.

10. The roll-on product of claim 1, comprising (by weight):
   water in a range of about 15-20%;
   magnesium hydroxide in a range of about 45-55%;
   propanediol in a range of about 17.5-22.5%;
   glycerin and *glycine soja* (soybean) in a range of about 3.5-5%;
   plant-derived components in a range of about 3.5-9.5%.

11. The roll-on product of claim 10, comprising (by weight):
   the magnesium hydroxide slurry 49.5-50%
   propanediol 17.5-22.5%
   glycerin and *glycine soja* (soybean) 3.5-5%.

* * * * *